(12) United States Patent
van Dun

(10) Patent No.: US 9,750,205 B2
(45) Date of Patent: Sep. 5, 2017

(54) QUARTET BREEDING

(71) Applicant: RIJK ZWAAN ZAADTEELT EN ZAADHANDEL B.V., De Lier (NL)

(72) Inventor: Cornelis Maria Petrus van Dun, De Lier (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 177 days.

(21) Appl. No.: 13/774,705

(22) Filed: Feb. 22, 2013

(65) Prior Publication Data

US 2013/0239251 A1  Sep. 12, 2013

Related U.S. Application Data

(63) Continuation-in-part of application No. PCT/EP2012/069191, filed on Sep. 28, 2012.

(30) Foreign Application Priority Data

Sep. 29, 2011 (EP) .................................... 11183362

(51) Int. Cl.
| | |
|---|---|
| *A01H 1/02* | (2006.01) |
| *C12N 15/82* | (2006.01) |
| *C12N 15/113* | (2010.01) |
| *A01H 1/04* | (2006.01) |
| *A01H 1/08* | (2006.01) |
| *A01H 3/04* | (2006.01) |
| *A01H 5/10* | (2006.01) |
| *C12N 15/62* | (2006.01) |

(52) U.S. Cl.
CPC ................ *A01H 1/02* (2013.01); *A01H 1/04* (2013.01); *A01H 1/08* (2013.01); *A01H 3/04* (2013.01); *A01H 5/10* (2013.01); *C12N 15/82* (2013.01); *C12N 15/62* (2013.01); *C12N 15/8212* (2013.01); *C12N 15/8218* (2013.01); *C12N 15/8287* (2013.01)

(58) Field of Classification Search
None
See application file for complete search history.

(56) References Cited

U.S. PATENT DOCUMENTS

| | | | |
|---|---|---|---|
| 2006/0179498 A1* | 8/2006 | Dirks ........................ | A01H 1/00 800/14 |
| 2008/0098496 A1* | 4/2008 | Van Dun ................... | A01H 1/00 800/268 |
| 2011/0083202 A1* | 4/2011 | Chan ........................ | A01H 1/08 800/260 |

FOREIGN PATENT DOCUMENTS

| | | |
|---|---|---|
| WO | WO 03/017753 | 3/2003 |
| WO | WO 2006/094773 | 9/2006 |
| WO | WO 2011/044132 | 4/2011 |

OTHER PUBLICATIONS

Preuss et al, Science (1994) vol. 264 pp. 1458-1460.*
Francis et al, Plant Phys (2006) vol. 142 pp. 1004-1013.*
Laurie et al, Theoretical Applied Genetics (1988) vol. 76 pp. 393-397.*
Wang et al. Chromosoma 120: 353-365 (2011).*
Carlson et al. Sexual Plant Reproduction 22: 257-262 (2009).*
Ravi et al. Nature 464: 615-619 (2010).*
Rhee et al. Plant Physiology 133(3): 1170-1180 (2003).*
Stacey et al. The Plant Journal 48: 206-216 (2006).*
Bhatt et al. The Plant Journal 19(4): 463-472 (1999).*
Bai et al. The Plant Cell 11: 417-430 (1999).*
Dirks, Rob et. al., "Reverse breeding: a novel breeding approach based on engineered meiosis", Plant Biotechnology Journal, Oxford, vol. 7, No. 9, Dec. 2009, p. 837-845.
Copenhaver, Gregory P, et. al. "Tetrad analysis in higher plants. A budding technology", Plant Physiology, vol. 24, No. 1, Sep. 2000, p. 7-15.
Preuss Daphne et. al, "Tetrad analysis possible in Arabidopsis with mutation of the Quartet (QRT) genes", Science, vol. 264, No. 5164, 1994, pp. 1458-1460.

* cited by examiner

*Primary Examiner* — David T Fox
(74) *Attorney, Agent, or Firm* — Vedder Price P.C.; Thomas J. Kowalski; Deborah L. Lu

(57) ABSTRACT

The invention relates to a method for the production of a set of seeds which are genetically identical to the male gametes from which they arise, which may comprise placing a limited number of paternal gametes that have the form of tetrads or dyads on the stigma of a flower to fertilize maternal egg cells to obtain a number of zygotes; and inducing the loss of maternal chromosomes from the zygotes to obtain a seed set containing a limited number of seeds in which the maternal chromosomes are absent. In a preferred embodiment the father plant exhibits suppression of chromosome recombination or second division restitution (SDR) during meiosis.

8 Claims, 4 Drawing Sheets

| Probability | | # of non-complementary chromosomes | | | | | | | | | | | | |
|---|---|---|---|---|---|---|---|---|---|---|---|---|---|---|
| n | 2^n | 0 | 1 | 2 | 3 | 4 | 5 | 6 | 7 | 8 | 9 | 10 | 11 | 12 |
| 2 | 4 | 50,0 | 50,0 | 0 | 0 | 0 | 0 | 0 | 0 | 0 | 0 | 0 | 0 | 0 |
| 3 | 8 | 25,0 | 75,0 | 0 | 0 | 0 | 0 | 0 | 0 | 0 | 0 | 0 | 0 | 0 |
| 4 | 16 | 12,5 | 50,0 | 37,5 | 0 | 0 | 0 | 0 | 0 | 0 | 0 | 0 | 0 | 0 |
| 5 | 32 | 6,3 | 31,3 | 62,5 | 0 | 0 | 0 | 0 | 0 | 0 | 0 | 0 | 0 | 0 |
| 6 | 64 | 3,1 | 18,8 | 46,9 | 31,3 | 0 | 0 | 0 | 0 | 0 | 0 | 0 | 0 | 0 |
| 7 | 128 | 1,6 | 10,9 | 32,8 | 54,7 | 0 | 0 | 0 | 0 | 0 | 0 | 0 | 0 | 0 |
| 8 | 256 | 0,8 | 6,3 | 21,9 | 43,8 | 54,7 | 0 | 0 | 0 | 0 | 0 | 0 | 0 | 0 |
| 9 | 512 | 0,4 | 3,5 | 14,1 | 32,8 | 49,2 | 0 | 0 | 0 | 0 | 0 | 0 | 0 | 0 |
| 10 | 1024 | 0,2 | 2,0 | 8,8 | 23,4 | 41,0 | 50,0 | 0 | 0 | 0 | 0 | 0 | 0 | 0 |
| 11 | 2048 | 0,1 | 1,1 | 5,4 | 16,1 | 32,2 | 45,6 | 45,6 | 0 | 0 | 0 | 0 | 0 | 0 |
| 12 | 4096 | 0,05 | 0,6 | 3,2 | 10,7 | 24,2 | 38,9 | 45,6 | 0 | 0 | 0 | 0 | 0 | 0 |

Figure 2

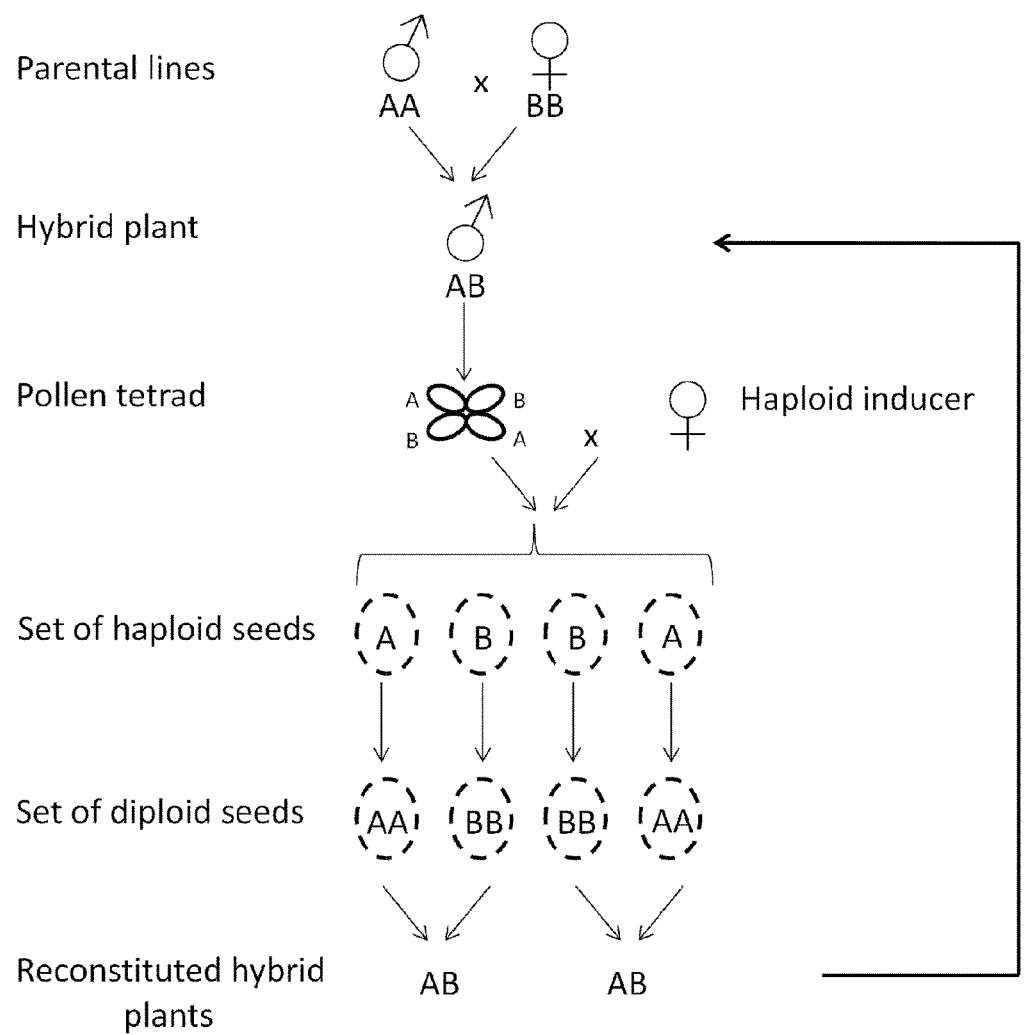

SEQUENCE LISTING

<160> NUMBER OF SEQ ID NOS: 1

<210> SEQ ID NO 1
<211> LENGTH: 2205
<212> TYPE: DNA
<213> ORGANISM: Arabidopsis thaliana

<400> SEQUENCE: 1
gctacataga gaggctccaa gtatttatta aactcatctt tctcacacga cctttcacct    60

```
ccaaagactc ccaacaaaaa tcataataaa gaaatacaaa aacgtaaact tgccaagtt      120 ttttttttctt cctttcttta actctctcac tcccacgaat tcgtgagaag aaaccttaaa    180
acgttttttt tccagagcac gaaaaaactc cccacctcac ttaaactttt ttccttgtgc     240
aggagacatc attccccatg aaagtcgaag cttttattcc cgccgtttta ttgctctgtt     300
ttggggtaat gttatgttta aaaagctcgt gtgcgttgca gataggtaac aataatgagt     360
tgaagaatta cataagttgg gaagatttga gagttgtgga agatggaaga atagagagaa     420
gttttagcat taaggagaat agtaattggg taaccacaaa cgctaacgct aacgcgaacg     480
ctactaacgt gagaagagtg attgtggttg ataaaaacgg aggaggagat tctgttacag     540
ttcaaggagc tgttgatatg gttcctgatt ccaattcaca gagagttaaa atcttcattc     600
ttcctgggat ttacaggtaa cttacaaaaa agatttaag acataaaccg tgtttgtttt      660
tttctttgta tgttattaat ctttgagaaa cgtctttggg agtgtggggt tttgtttccg     720
aagatttcgt tttttttttt gtttttttt ggtgtgataa aagcagttga agctaaattc      780
ttgggttagt gggataatct aagcataagc tgcttacgta aataaaatcg tgggtctcaa     840
gaatctttgt ctgtaaaacc gtagaataag aatctttgtc tttgttatat actctgttct    900 tttttttgtca gaatctttgt ctttgttatc tactcttgtt ttttttcttc agaatctctt   960
ctctgctatg tgttgtttgc agggagaagg tgattgtgcc gaaatcaaaa ccgtatattt    1020
cgttcatagg taatgagagc tatgcgggag atacagtgat tagttggagc gataaagctt    1080
cagaccttgg ctgcgatggt aaagaactcg gcacttatag aaccgcctct gtttccattg    1140
aatctgattt cttctgtgct actgccatca cttttgaggt cctaaaaccc tctcttttac    1200
tattattcct tgtctacttt ctatgtgtat tgtgttttta tgttttgaat tgtttgtgat    1260
gtacggattg aggcagaaca cggtggttgc agaggcaggg gaacagggga ggcaagcggt   1320
ggcgttgaga ataattgggg acaaagctgt gttctataga gttagggttt tgggatcaca    1380
agacactctt tttgatgaca atggatctca ctactttttac caatgctata tccaaggcaa    1440
tgtagatttc atctttggca atgcgaaatc actttaccag gcaaaacccc ttccatttga    1500
tcttcttaaa tccttttgtat cgaaatccat ttgtaaagat attgatcgaa gttttggtgt    1560
ttggtaacca caggactgtg atatccactc aaccgcaaag agatatggcg cgatcgcggc   1620
tcatcataga gactcggaga ctgaagatac cgggttctcc tttgtgaact gtgatatcag    1680
tggtactggg cagatttact taggaagggc ttggggaaac tactcaagaa ctgtttattc    1740
aaactgtttc atagctgata ttatcactcc tgtgggctgg agtgactgga aacaccctga    1800
gaggcaaagg taaaaaaagg atcttgaaaa ttgaaaactc atctctgaaa ctacagcatt    1860
tctctctcaa aacaacatca agcgaatttc ttttgcagga aagtgatgtt cggggagtac    1920
aattgcaggg gaagaggagc agagagagga ggccgagtac cgtggtcgaa aactcttacc    1980
agagatgaag tgaagccttt tctgggaaga gagttcatat atggagatca atggctgaga    2040
ctctaaatcc tttttcaacc ggacataaag gtccagctag ctaacaggag atgatgatct    2100
aattctactc tattcatttg taattagttt gaatttagag agaaatagaa tctgcatgtt    2160
ttaactcata ccaaagtaaa tgaaacccag gttttggttt tagat                    2205
```

QUARTET BREEDING

RELATED APPLICATIONS AND INCORPORATION BY REFERENCE

This application is a continuation-in-part application of international patent application Serial No. PCT/EP2012/069191 filed 28 Sep. 2012, which claims benefit of European patent application Serial No. 11183362.0 filed 29 Sep. 2011.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted electronically in ASCII format and is hereby incorporated by reference in its entirety. Said ASCII copy, created on Apr. 21, 2017, is named 43104_00_2101_SL.txt and is 3,279 bytes in size.

FIELD OF THE INVENTION

This invention relates to a method for the production of a set of seeds which are genetically identical to the male gametes from which they arise. This invention further relates to a set of seeds containing a limited number of seeds in which the maternal chromosomes are absent, which set is composed of pairs of genetically complementary seeds which when plants grown from the seeds are crossed result in essentially the same hybrid. The invention also relates to a method for providing a set of parent plants for the production of a plant of which the genetic constitution is essentially identical to the genetic constitution of its male grandparent.

BACKGROUND

Plant breeding corresponds to the domestication of plant species for the benefit of humans to obtain food, feed and fiber of sufficient quality and quantity. Plant breeding is a very old occupation of mankind and only in the course of the 20$^{th}$ century has the practical knowledge received a scientific foundation. Plant breeding was originally based on selecting and propagating those plants that were outperforming in local selection fields. With the rediscovery of the genetic laws and the development of statistical tools plant breeding became based on knowledge of genetics and was technologically supported by methods such as doubled haploids (DH)—see e.g. Haploids in Crop Improvement II eds; Palmer C, Keller W, and Kasha K (2005) in: Biotechnology in Agriculture and Forestry 56 Eds; Nagata T, Lörz H, and Widholm J. Springer-Verlag Berlin Heidelberg New York, ISBN 3-500-22224-3—and molecular markers—see e.g. De Vienne ed. (2003) Molecular Markers in Plant Genetics and Biotechnology. Science publishers Inc. Enfield, N.H. USA. ISBN 1-57808-239-0.

Plant breeding delivers genetic concepts tailored to a specific environment which allows its exploitation in an economic manner. This objective of plant breeding is achieved through the efficient utilisation of genetic variation which exists within the germplasm of plant species. Such genetic concepts comprise combinations of genes which lead to a desirable phenotype in a particular environment. This means that the plant parts which are harvested are maximised in yield and quality, at the lowest possible cost required to grow the plants and harvest the product. When plant breeding is applied at a commercial level, seed production is also an important issue. Seed production aims at the multiplication of plants by means of sexual reproduction, in which the genetic composition is preserved.

In addition, the commercial seeds need to be of sufficient quality to allow efficient germination. The preservation of genetic constitution through sexual reproduction is however a paradox, because sexual reproduction fundamentally exists to create offspring with new combinations of alleles. The genetic mechanisms that act during sexual reproduction have evolved to increase genetic variation, in order to enhance the chances of survival of a species in a changing environment. Meiotic recombination, independent chromosome assortment and the mating system are main contributing factors in this respect. Uniformity in offspring through sexual reproduction can therefore only be achieved when the parental plants are fully homozygous. Combining gametes of such plant will lead to the exact reproduction of the genetic composition of the parent in each subsequent generation.

In many crops, the commercial seeds result from a cross of two homozygous parental lines. This approach ensures that the F1 hybrid is heterozygous for several loci, which can result in hybrid vigour and uniformity. If a breeder wishes to improve an existing F1 hybrid variety or an inbred variety, he will traditionally need to make crosses and go through several rounds of empirical selection to achieve this objective.

As the knowledge of gene function in relation to plant growth and development is still limited, breeders still largely depend upon phenotypic selection. As during inbreeding many genes are in a heterozygous state, especially during early generations, the allelic variants of the genes responsible for the phenotypic value assigned to some of the individual plants can be lost easily. This is due to the fact that during sexual reproduction and inbreeding heterozygosity and specific gene interactions are lost. Therefore, in plant breeding these mechanisms may act counterproductively, especially in those cases where genetically heterozygous plants have been identified with high agronomic, horticultural or ornamental value. Sexual reproduction will result in the segregation of the desirable alleles.

Therefore there is a strong need for technology that efficiently allows the preservation of the genetic constitution during sexual reproduction of plants with a high agronomic, horticultural or ornamental value.

One possibility to perpetuate plants while preserving the genetic constitution is by vegetative propagation. This allows a complete preservation of the genetic composition, as multiplication occurs exclusively through mitosis. Plants have evolved natural mechanisms of vegetative propagation, which allow them to swiftly occupy habitats. For example, vegetative propagation can occur through the formation of tubers, bulbs or rhizomes. An alternative is to use in vitro or in vivo culture technology to produce cuttings. A commercial disadvantage of vegetative propagation technology, when compared to propagation through seeds, is the fact that it is labour-intensive and therefore costly. Furthermore, it is difficult to store plants for longer periods of time, which poses logistic problems, and the risks of infections of the plant material with pathogens like viruses is considerably larger as compared to a situation in which plant material is propagated through seeds.

Alternatively, vegetative propagation may be achieved through the formation of asexual seeds, which is generally referred to as apomixis. This phenomenon occurs naturally in a number of species, and it may be induced in sexually propagating plant species by genetic engineering. In theory, this can be achieved by making use of specific genes which naturally induce the three different steps of apomixis, i.e. apomeiosis, parthenogenesis and autonomous endosperm development. In practice, however, the genes responsible for the different steps have not yet been identified, and their interaction may be quite complicated.

On the other hand, artificial engineering of the apomixis components may be quite feasible. For example, by modifying different steps during meiosis it has been shown that meiosis can be essentially converted into mitosis. This so-called "MiMe approach" makes use of a combination of mutations which suppress double strand break formation (spo11-1), induce sister chromatid segregation during meiosis I (rec8) and skip the second meiotic cell division (osd1). Combining this approach with parthenogenesis and autonomous endosperm formation may ultimately result in engineered apomixis (d'Erfurth et al: Turning meiosis into mitosis; PLoS Biology 2009; WO/2010/079432). Although since long the potential of apomixis technology for plant breeding has been widely recognised, proof of concept is still not available.

As yet another alternative, use can be made of reverse breeding technology (WO03/017753). Reverse breeding is based on the suppression of meiotic recombination through genetic engineering or chemical interference, and the subsequent production of doubled haploid plants (DHs) derived from spores containing unrecombined parental chromosomes. These DHs differ with respect to their genetic composition solely as a consequence of the independent parental chromosome assortment which occurs during meiosis. Therefore, it is sufficient to make use of one co-dominant, polymorphic marker per chromosome to determine which of the DHs or lines derived thereof should be combined through crossing to reconstruct the genetic composition of the original starting plant. As such, application of reverse breeding technology allows genetic preservation of any fertile selected plant through seeds, even if its genetic composition is unknown.

A disadvantage of this technology is the fact that complete suppression of meiotic recombination results in the absence of chiasmata. This may lead to inappropriate chromosome segregation during meiosis I, which can lead to aneuploidy of the gametes and thus to reduced gamete viability and performance. When no chiasmata are formed during meiosis I, every chromosome has an independent 50% chance to move to either one of the poles. This means that the theoretical chance to make a spore with a full chromosome complement is $(\frac{1}{2})^n$, wherein n represents the haploid chromosome number. The frequency of balanced gametes therefore decreases with increasing haploid chromosome number. Although many crop species have a relatively low chromosome number (e.g. cucumber has 7 chromosomes per haploid genome; spinach has only 6) there are also economically important species with relatively high chromosome numbers. A good example is tomato, economically one of the most important vegetable crops, which has 12 chromosomes per haploid genome. This technical constraint significantly reduces the efficiency of reverse breeding technology.

As another alternative approach use can be made of plants regenerated from unreduced spores. This technology has been termed Near Reverse Breeding (WO2006/094773). The unreduced spores are formed preferentially as a consequence of the omission of the second meiotic division. This naturally occurring phenomenon is known as Second Division Restitution (SDR), and it can occur in plants during sexual reproduction concomitantly with regular meiotic events.

Near Reverse Breeding technology exploits SDR events by regenerating plants from unreduced spores, produced through natural or engineered SDR. Genes have been discovered which—when mutated—give rise to SDR, such as OSD1 and TAM1. The resulting plants (termed SDR-0 plants) are largely homozygous, and they can be subsequently used to produce traditional DHs. Molecular markers which are polymorphic between the paternal and maternal genomes of the starting plant can be used to identify those SDR-0 plants (and DHs derived thereof) that are largely complementary with respect to their genetic composition.

Crossing of these plants will result in the near-complete reconstruction of the genetic make-up of the original starting plant. However, due to meiotic recombination during the formation of the SDR-0 events and during the formation of the DHs derived thereof, the complementarity will not be complete. The reconstructed hybrids will genetically differ to some extent, both from each other and from the original starting hybrid plant. However, this variation will be strongly reduced when compared to a situation in which the DHs are derived directly from a regular meiotic event. Moreover, these DHs are genetically fixed, which means there is no room for further selection.

The advantage of integrating an SDR event in this process is that the selection for genetic complementarity occurs in a two-step process. The first step is concentrated on the proximal regions of the chromosomes, i.e. including the centromeres. The second step is directed towards the distal ends of the chromosomes, i.e. those regions which were exchanged due to recombination. This delayed genetic fixation reduces the complexity and increases the chances of finding largely complementary genotypes, especially when molecular markers are available for selection.

A further advantage of this approach is the fact that SDR can occur naturally during sexual reproduction and that it can be exploited as such without further need to interfere with sexual reproduction processes. Methods to further increase the normal prevalence of SDR events are known in the art, for example through stress treatment with $N_2O$ (as has previously been described in lily: Barba-Gonzalez et al (2006), Euphytica 148: 303-309; and in tulip: Okazaki et al. (2005), Euphytica 143: 101-114).

Citation or identification of any document in this application is not an admission that such document is available as prior art to the present invention.

SUMMARY OF THE INVENTION

It is an object of the present invention to further increase the efficiency of the above-described methods for preserving the genetic constitution of a heterozygous plant with excellent agronomic, horticultural or ornamental properties.

The present invention takes advantage of the observation that specific mutations may lead to a defect in the separation of microspores during pollen formation. This results in the formation of clusters of four pollen grains which remain physically attached together throughout their development. Although the individual pollen grains in the clusters remain together in a tetrad at maturity, they are fertile and may each perform fertilisation and produce seeds upon pollination. The biological explanation for this so-called quartet phenotype is the failure to dissolve the pectin layer which is normally only present between the microspores, in the early stages of pollen development.

The invention thus relates to a method for the production of a set of seeds which are genetically identical to the male gametes from which they arise, which may comprise:
a) placing a limited number of paternal gametes that have the form of tetrads or dyads on the stigma of a flower to fertilize maternal egg cells to obtain a number of zygotes;
b) inducing the loss of maternal chromosomes from the zygotes to obtain a seed set containing a limited number of seeds in which the maternal chromosomes are absent.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIG. 2: this table shows the probability (percent chance) of finding a certain degree of complementarity in the four members of a pollen tetrad, as a function of the haploid chromosome number. For e.g. cucumber (with n=7) the chance of encountering meiotic products having 0, 1, 2 or 3 non-complementary chromosomes (and hence with 7, 6, 5 or 4 complementary chromosomes, respectively) within a pollen tetrad of cucumber is thus 1.6% (=(1+1)/128), 10.9% (=(7+7)/128), 32.8% (=(21+21)/128) and 54.7% (=(35+35)/128), respectively.

The probability (percent chance) of finding a certain degree of complementarity in the four members of the quartet is given by the table in FIG. 2. The chance of encountering meiotic products having 0, 1, 2 or 3 non-complementary chromosomes (and hence with 7, 6, 5 or 4 complementary chromosomes, respectively) within a pollen tetrad of cucumber is thus 1.6% (=(1+1)/128), 10.9% (=(7+7)/128), 32.8% (=(21+21)/128) and 54.7% (=(35+35)/128), respectively.

Figure 3:
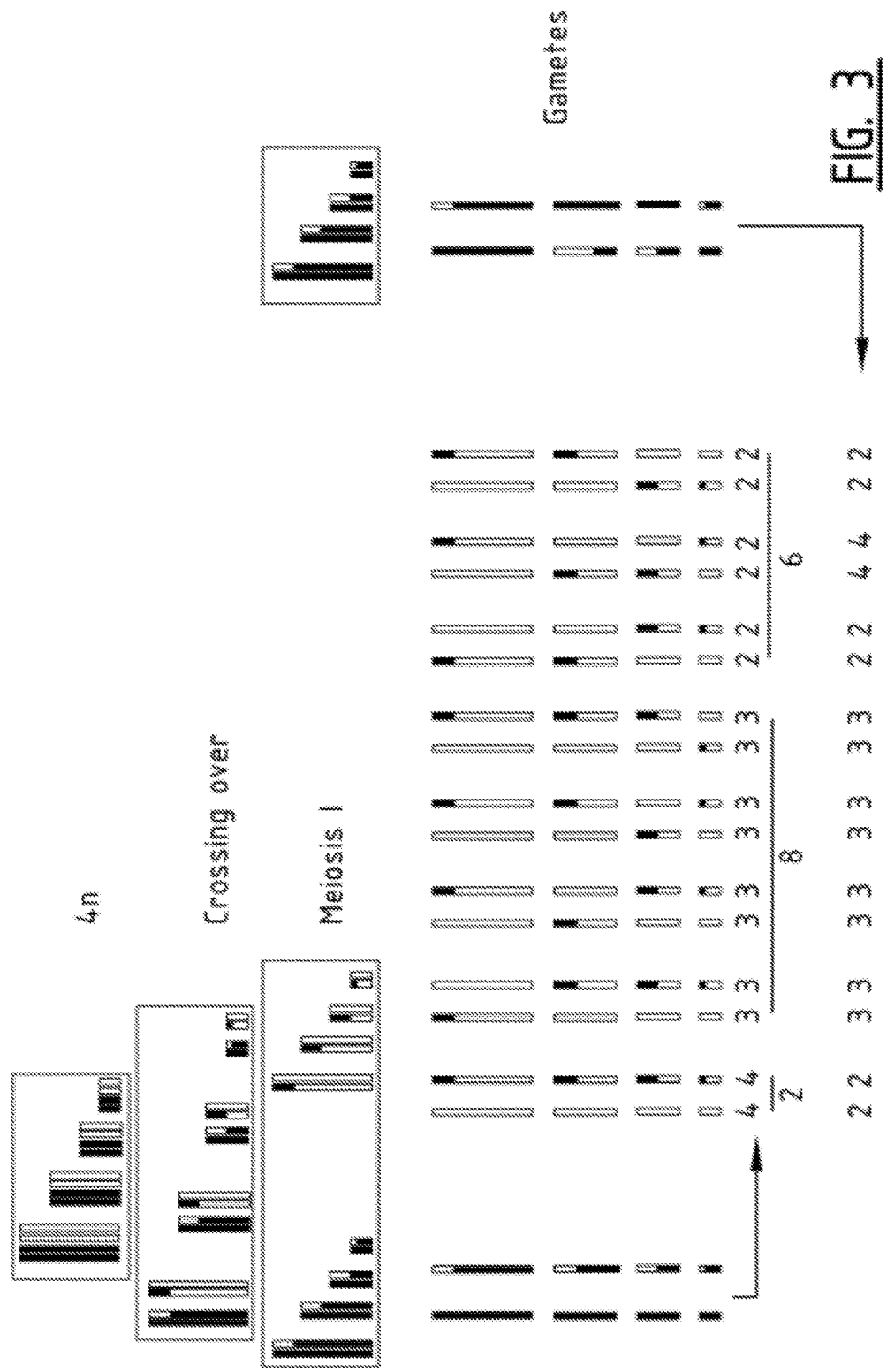

FIG. 3: graphical representation of a meiotic event with 4 haploid chromosomes (n=4). One parent of the hybrid plant contributed black chromosomes, while the other parent contributed white chromosomes to the hybrid. In a first step the genome doubles from 2n to 4n, and subsequently crossing-over can take place between the homologous regions of sister chromatids, as illustrated here with a single cross-over event per chromosome. During the first meiotic division two diploid daughter cells are produced, which are genetically completely complementary (i.e. if both their genomes are taken together the 4n genomic composition from before the division is obtained). In this figure only one possible example of the outcome of meiosis I is shown. During the second meiotic division the gametes (in this context: microspores or pollen grains) are produced, and the chromosomes can randomly segregate to either daughter cell. This leads to $2^{n-1}$ different pairs of daughter cells (gametes). For the diploid cell on the left the figure shows one possible pair of gametes, while for the diploid cell on the right all 8 possible pairs of gametes are shown (=$2^3=2^{n-1}$).

When subsequently doubled haploid plants are regenerated from the different gametes (for example by the method of the invention, by generating haploid plants and doubling their genome), these plants can be crossed to each other. The numbers just below the different chromosome sets correspond to the number of chromosomes that are complementary to the chromosome set on the far left of the figure. If for example the plant containing the four chromosomes that are depicted on the far left (i.e. the four black chromosomes) would be crossed to a plant containing the four entirely white chromosomes from the first of the eight chromosome pairs on the right, then all 4 chromosomes would be complementary. This cross would result in the exact reconstitution of the original hybrid plant that had produced the gametes. Similarly, crossing the same plant with the four black chromosomes with plants containing the other possible chromosome sets displayed on the right (more precisely: the left chromosome set of each of the eight pairs) will either result in the complete reconstitution of the original hybrid plant (when all 4 chromosomes are entirely complementary), or in the near-complete reconstitution of the original hybrid plant (when one or two of the four chromosomes are not entirely complementary). The situation that more than two chromosomes would not be complementary does not exist, because the gametes originated from the same meiotic event. In addition, it is clear from the drawing that a large part of the "non-complementary" chromosomes is in fact complementary, and that crossing will lead to a highly heterozygous progeny; the only non-complementary chromosome parts are due to the cross-over events at the chromosomes' telomeres, which cross-over regions would become homozygous in the resulting progeny. When the numbers below the chromosome pairs are added up to group the events that have 0, 1 or 2 non-complementary chromosomes in comparison to the chromosome set on the far left, this leads to the 2-8-6 distribution for n=4, which can also be found in the fourth row of the triangle of FIG. 1 (where they are displayed as 1-4-6-4-1).

On the far right of this figure a second possible pair of gametes is depicted, that can be derived from the left-most diploid cell during meiosis II. The numbers listed at the bottom of the figure represent the number of complementary chromosomes when one of the gametes from this pair is combined with any of the 16 gametes derived from the right-most diploid cell. Again the same outcome can be observed: of the 16 gametes 2 are fully complementary (i.e. 4 complementary chromosomes), 8 have one non-complementary chromosome and 6 have two non-complementary chromosomes. By keeping the four products derived from a single meiotic event together, and by providing a means to obtain progeny plants that are genetically identical to these four meiotic products, the present invention maximizes the chance of identifying pairs of progeny plants that upon crossing can give rise to the original hybrid plant, or to a hybrid that is genetically essentially the same as the original hybrid.

Figure 1:
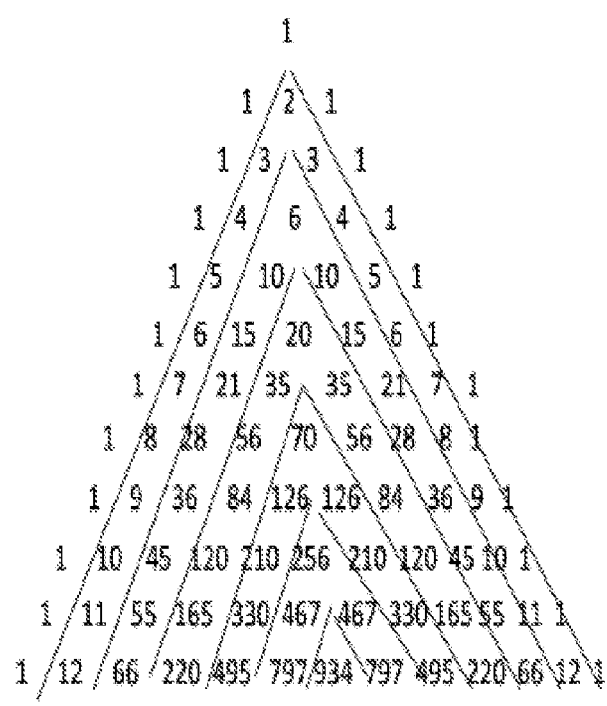
FIG. 1: the so-called Pascal's Triangle, depicting the specific outcome of chromosome complementarity for each pollen tetrad, in function of the number of chromosomes of the species. From top to bottom the number of haploid chromosomes increases, and the sum of the numbers on each row always equals $2^n$, being the total number of different meiotic products that can arise from a meiosis in which n chromosomes are involved. If we take the seventh row as an example (for e.g. cucumber, with 7 haploid chromosomes, n=7), it can be seen that the number of fully complementary events is always 1, i.e. the first number on the row, while the second number on the row corresponds to the number of haploid chromosomes. The subsequent numbers in the same row correspond to the expected number of meiotic products having 2, 3, 4, 5 and 6 non-complementary chromosomes in a tetrad, respectively. The total number of events with one non-complementary chromosome is 7*2, with two non-complementary chromosomes 21*2, etc. If e.g. 3 chromosomes are non-complementary, this implies that the other four chromosomes are complementary. Importantly, "non-complementary" in this context actually only refers to the telomeric ends of these chromosomes. If we e.g. have a situation with 3 non-complementary chromosomes and only 40% heterozygosity after recombination, 4 of the 7 chromosomes will be completely complementary, while the other 3 chromosomes are still 60% complementary.

FIG. 4: simplified overview of a pedigree according to the present invention, assuming that no recombination occurs. A hybrid plant, resulting from the cross of two (homozygous) parental lines (with genotypes AA and BB, respectively) produces pollen grains in the form of tetrads. When a single tetrad is used to pollinate a haploid inducer mother plant (with random genotype) the progeny resulting from this cross will consist of a set of four haploid seeds. Genetically these seeds are A, A, B and B (in the absence of recombination), and there is no genetic contribution from the mother plant. Hence these four haploid seeds only have two grandparents, namely the parental lines of the hybrid father plant that produced the pollen tetrad. After genome doubling four doubled haploid plants can be obtained, which—in the absence of recombination—will always be pairwise genetically fully complementary. Crossing the two genetically complementary plants from any of the pairs leads to the reconstitution of the original hybrid plant. The situation is more complex when recombination does occur, as illustrated by FIGS. 1, 2 and 3. When recombination occurs the chance of finding a pair of fully complementary plants among the progeny of a pollen tetrad decreases in function of the haploid chromosome number, but in the absence of recombination the chromosome number has no effect on the outcome.

DETAILED DESCRIPTION OF THE INVENTION

"Genetically identical" means that all chromosomes of one seed are the same as the chromosomes of the corresponding gamete and the combination of chromosomes within a seed is the same as in the corresponding gamete.

In the research leading to the present invention it was furthermore surprisingly found that combining methods available in the prior art with the above specific mutations that lead to a defect in the separation of microspores during pollen formation leads to a great increase in the efficiency with which parent plants with an essentially complementary genetic constitution may be identified, which after crossing will give rise to a heterozygous plant with essentially the same genetic constitution as its paternal grandfather. Such methods with which the invention may be combined are for example reverse breeding and near reverse breeding.

The quartet phenotype was for example described in Copenhaver et al (2000) Plant Physiology 124, 7-15. Mutations in different non-homologous genes may result in similar quartet phenotypes (e.g. qrt1, qrt2 and qrt3 in *Arabidopsis thaliana*). The QRT3 gene (in *Arabidopsis*: At4g20050) has been molecularly characterised, and it encodes a member of a divergent class of polygalacturonases (Rhee et al. (2003) *Plant Physiology* 133: 1170-1180). These mutations are useful for providing the tetrad for use in the method according to the invention.

The individual pollen grains in the clusters of four pollen grains contain the products of a single meiotic cell division. When an individual pollen quartet is used to fertilise a plant, this ideally leads to the formation of 4 seeds, when the efficiency of fertilisation is 100%. The fact that the four individual pollen grains of a tetrad represent the products of a single meiotic cell division has interesting implications for the technology which is subject of this invention.

At the start of meiosis, the initial process is the replication of the genomic DNA. Subsequently, during prophase homologous chromosomes align and synaps, to form the bivalents. During this stage double strand breaks (DSBs) are formed which are repaired using the aligned non-sister chromatids. The chromosomal interaction during repair leads to the formation of specific structures called double holiday junctions, which are resolved. This leads either to gene conversion or crossing over. The crossing over (CO) events are ultimately visible in the form of chiasmata, which are structurally required for appropriate homologue segregation during meiosis I. With respect to this invention it should be noted that irrespective of the distribution of the COs the products of meiosis I are always fully complementary with each other, with respect to their allelic composition. During the second meiotic division the sister chromatids segregate to opposite poles, giving rise to the final meiotic products, i.e. four haploid cells. Normally these four meiotic products become detached from each other during their further development, and they will mingle with the pollen grains derived from other meiotic events inside the same anther locule. However, when the mother plant exhibits the quartet phenotype, the four products of a single meiotic event will physically remain together.

The set of four pollen grains in a tetrad may contain variable degrees of genetic complementarity, which is a function of the number of haploid chromosomes. As the products of meiosis I are fully complementary among each other, the four pollen grains held together in the tetrad contain at least 50% complementarity. The specific outcome for each tetrad is determined by chance, and this chance follows a distribution which is given by the so-called Pascal's Triangle (FIG. 1).

For example, cucumber has 7 haploid chromosomes. The first meiotic division results in two fully complementary meiotic products. During the second meiotic division the chromosomes may segregate randomly in each of the two products of meiosis I, which may result in $2^n=2^7=128$ different products. In general, it may be stated that in case of N chromosomes, a total of $2^n$ different tetrads may be obtained from a single meiotic event. The number of fully complementary events is always 1, i.e. the first number on each row (FIG. 1), while the second number on each row corresponds to the number of haploid chromosomes. The subsequent numbers in the same row correspond to the expected number of meiotic products having 2, 3, 4, 5 and 6 non-complementary chromosomes in a tetrad, respectively.

In the example of cucumber, with 128 different meiotic products originating from any given meiotic event, these numbers are 21, 35, 35, 21 and 7, respectively. As the products of meiosis I are fully complementary to each other, the extreme situation that none of the chromosomes would be complementary does not exist within a tetrad, because there will always be complementarity to the chromosomes of the other meiosis I product. The number of events with one non-complementary chromosome is therefore 7*2, with two non-complementary chromosomes 21*2, etc. If e.g. 3 chromosomes are non-complementary, this implies that the other four are complementary. The probability (percent chance) of finding a certain degree of complementarity in the four members of a pollen tetrad is given by the table in FIG. 2. The chance of encountering meiotic products having 0, 1, 2 or 3 non-complementary chromosomes (and hence with 7, 6, 5 or 4 complementary chromosomes, respectively) within a pollen tetrad of cucumber is thus 1.6% (=(1+1)/128), 10.9% (=(7+7)/128), 32.8% (=(21+21)/128) and 54.7% (=(35+35)/128), respectively.

Importantly, "non-complementary" in this context actually only refers to the telomeric ends of these chromosomes. If we e.g. have a situation with 3 non-complementary chromosomes and only 40% heterozygosity after recombination, 4 of the 7 chromosomes will be completely complementary, while the other 3 chromosomes are still 60% complementary. In essence, the tetrad constellation thus results in a situation in which the pollen grains are always pairwise at least entirely complementary for 50% of the chromosomes, and—as a result of recombination—still partially complementary for the remaining chromosomes. This invention thus accomplishes the near-complete reconstitution of the genotype of a hybrid plant, while still allowing between 0 and 50% of variation compared to the original hybrid plant from which the pollen tetrads are derived to carry out the invention.

This method therefore allows the reconstruction of the identical or near-identical genetic constitution of a hybrid plant. The near-identical reconstruction has definite advantages, as this allows the evaluation of the effect of additional genetic variation on the hybrid phenotype of interest. This additional genetic variation may either prove to have an advantageous or disadvantageous effect on the hybrid phenotype, and this will allow for the further genetic improvement of a superior hybrid phenotype. The situation for four chromosomes is graphically illustrated in FIG. 3.

An important aspect of the claimed invention is the use of quartet microspores for the pollination of a mother plant which eliminates the maternal genome from its hybrid progeny. An example of such a plant has been recently described in *Arabidopsis* by Maruthachalam and Chan (*Haploid plants produced by centromere-mediated genome elimination; Nature* 464 (2010), 615-619; US patent application 20110083202; WO2011044132), but this example is in no way limiting the application of this invention, as the invention may also be carried out with other haploid inducer systems.

The elimination of the maternal genome from hybrid progeny may thus be achieved by means of transgenic replacement of the endogenous centromere-specific histone protein CENH3 by a modified version. In practice, a modified version of the CENH3 protein is overexpressed in a plant that lacks a functional endogenous CENH3 gene.

Alternatively, also the CENPC, MIS12, NDC80 or NUF2 polypeptides may be used for the same purpose, when overexpressed in a plant that has a corresponding inactivated endogenous CENPC, MIS12, NDC80 or NUF2 gene. Suitably one or two alleles of the endogenous CENH3, CENPC, MIS12, NDC80 or NUF2 genomic coding sequence of the plant is inactivated or knocked-out, and preferably all alleles are inactivated or knocked-out. The plant, when crossed with a wildtype plant, generates for example at least 0.1% haploid progeny.

Preferably the polypeptide is a recombinantly altered CENH3 polypeptide. The polypeptide may comprise a heterologous amino acid sequence of at least five amino acids (or alternatively of at least ten amino acids) linked to a protein which may comprise a CENH3 histone-fold domain, wherein the amino acid sequence is heterologous to the CENH3 histone-fold domain. Suitably, the said heterologous amino acid sequence is linked directly to the CENH3 histone-fold domain and the polypeptide lacks a CENH3 tail domain. Alternatively, the heterologous amino acid sequence may be linked to the CENH3 histone-fold domain via an intervening protein sequence. This intervening protein sequence may comprise a CENH3 tail domain or a non-CENH3 histone H3 tail domain (and the recombinant protein then corresponds to a tail-swap version of the CENH3 protein).

Suitably, when the intervening protein may comprise a CENH3 histone H3 tail domain, the CENH3 tail domain may be heterologous to the CENH3 histone-fold domain. When the polypeptide may comprise a CENH3 histone-fold domain and a truncated CENH3 tail domain, the amino terminus of the tail domain is truncated relative to the plant's endogenous tail domain.

Pollinating such transgenically complemented plants with pollen from a wildtype father plant results in sterile progeny, due to the fact that the F1 progeny is haploid. In fact each F1 progeny is genetically identical to the pollen grain that was used for fertilization and from which it originated. Wild type and modified chromosomes are apparently incompatible in kinetochore assembly in the zygote. Spontaneous or induced doubling of chromosomes leads to the formation of DHs. CENH3 is a conserved and probably single copy gene in plants, and this system may therefore also be applied in crop species. If seed formation would be problematic due to endosperm imbalance, embryo rescue may be performed.

In another embodiment, the maternal genome may be eliminated from the F1-progeny by means of other haploid inducer systems, or through interspecies crossing (as described by e.g. Bains & Howard 1950, *Nature* 166: 795).

In a further embodiment, the quartet mutation may also be combined with reverse breeding technology (WO03/017753; Dirks et al. 2009, *Plant Biotech J* 7: 837-845), thereby greatly improving the efficiency of reverse breeding. In this embodiment, the quartet phenotype is combined with suppression of meiotic chromosome recombination in the father plant, by genetic, transgenic or chemical means. While the quartet mutation results in the physical attachment of the 4 products of a single meiosis in a tetrad at pollen maturity, the suppression of recombination ensures that these pollen grains contain unrecombined parental chromosomes. The present invention thus ensures that DHs with complementary genetic composition may easily be identified among the four DHs derived from pollen from a single meiosis, with one co-dominant, polymorphic marker per chromosome.

A drawback of reverse breeding may be the occurrence of unbalanced (aneuploid) spores. It is however possible to morphologically identify balanced tetrads (for example by visually selecting tetrads in which the four pollen grains are equal in size, which is indicative of an equal distribution of all chromosomes, or by means of e.g. flow cytometry), and DHs regenerated from such tetrads will automatically be pairwise complementary. When balanced tetrads are used for pollinating a mother plant which eliminates the maternal genome from its hybrid progeny, this will give rise to 4 haploid seeds which are pairwise complementary with respect to their genetic composition. Subsequent crossing of the complementary DHs or lines derived thereof will result in the reconstruction of the genetic composition of the original starting plant. When the four progeny plants of this cross are not genotyped prior to crossing, the chance of obtaining a reconstruction of the genetic composition of the original starting plant by randomly crossing two of these four plants is 50%.

In another embodiment, the quartet phenotype may be combined with Near Reverse Breeding (WO2006/094773). In this embodiment, the occurrence of second division restitution (SDR) in a plant that exhibits the quartet phenotype will lead to the production of pollen dyads by the father plant, which may comprise two diploid pollen grains with a perfectly complementary genetic composition, including identical chromosome breaking points. Pollinating a mother plant that eliminates the maternal genome from its hybrid progeny with such a pollen dyad will result in two diploid plants, and crossing these two plants with each other will result in the near-complete reconstitution of the genetic composition of the original hybrid.

"Near-complete" refers in this application to the fact that together the two plants have the same genetic material as their father plant (as no DNA is lost or gained during a meiotic division), but the relative genomic position of chromosomal segments may be different, as a result of cross-over events during meiosis. The position of chromosomal breakpoints is however identical in the two plants, as they originated from a single meiotic event. The identification of complementary SDR-0 lines is thus greatly facilitated by exploiting the quartet phenotype, and the near-complete reconstitution of the genetic composition of any given hybrid becomes much easier and efficient.

Due to meiotic recombination during the formation of the SDR-0 events the reconstitution will not be 100% complete, since the reconstructed hybrids will genetically differ to some extent, both from each other and from the original starting hybrid (father) plant, especially at the telomers as a result of COs. This feature thus provides the additional advantage that additional genetic variation is being created in a pre-selected superior hybrid plant, by providing alternative and slightly differing genomic arrangements while maintaining most of the original hybrid constitution. This may lead to a further improvement of a hybrid phenotype.

It is a further object of this invention to provide an efficient method for obtaining a set of seeds, which seeds are genetically identical to the male gametes from which they arise, and which set of seeds is composed of pairs of genetically essentially complementary seeds which, when the plants grown from them are crossed, give rise to essentially the same hybrid plant. This hybrid plant is genetically essentially identical to the plant that produced the male gametes from which the said set of seeds arose.

"Essentially" as used herein is intended to mean that the genetic complementarity of the pairs of seeds need not be 100%, as also the near-complete reconstitution of a hybrid plant may be desirable, as explained above (because it may offer the opportunity to further improve a hybrid phenotype). Such a near-completely reconstituted hybrid plant is only essentially identical to the original hybrid plant and to other near-completely reconstituted hybrid plants obtainable by the invention, because although it has the same or largely the same genomic material as the original hybrid plant, there may be alternative or slightly differing genomic arrangements present in their genomes, as a result of different cross-over events, or some genomic regions may be homozygous as a result of recombination. When meiotic cross-over takes place, "essentially" thus relates to the degree of cross-over that occurred during the formation of the pollen grains used for pollinating the haploid-inducer mother plant.

In another context, for example in the absence of meiotic recombination, "essentially" may also refer to the selection of pairs of seeds (from among the set of seeds obtained by this invention) that are not 100% genetically complementary to each other. In this embodiment, which is also intended to fall within the scope of the present invention, for example a pair of seeds may be selected (from the said set of seeds) that are fully complementary to each other for n-1 chromosomes (with n being the haploid chromosome number of the species), and identical for the remaining chromosome. The hybrid plant resulting from the cross of the plants grown from this pair of seeds will then be genetically identical to the original hybrid plant for all but one chromosome, and different (namely homozygous) for the remaining chromosome. Overall the plant is thus only "essentially" genetically identical. Such plants may for example be obtained when carrying out the present invention in a preferred embodiment, with suppression of meiotic recombination ("Reverse Breeding"). It is to be understood that the same concept may be done for n-2 chromosomes, n-3 chromosomes, etcetera. This concept allows, for example, the genomic and phenotypic analysis of a plant while focusing on only a subset of its chromosomes, and while leaving the rest of the hybrid genome unchanged.

The invention thus relates to a method for the production of a set of seeds which are genetically identical to the male gametes from which they arise, which may comprise:
a) placing a limited number of paternal gametes that have the form of tetrads or dyads on the stigma of a flower to fertilize maternal egg cells to obtain a number of zygotes;
b) inducing the loss of maternal chromosomes from the zygotes to obtain a seed set containing a limited number of seeds in which the maternal chromosomes are absent.

In this method competition among pollen tubes for the fertilization of ovules should preferably be minimized or prevented, to avoid that some of the pollen grains comprised in a tetrad or dyad fail to fertilize an ovule. Therefore a limited pollination is preferable, such that there are at least as many ovules present in the female reproductive organ of the pollinated flower as there are pollen grains deposited onto its stigma. Each pollen grain should then be able to fertilize an ovule.

In one embodiment, the limited number of paternal gametes is therefore equal to or lower than the number of egg cells contained in the female reproductive organ carrying the stigma.

The average number of egg cells or ovules per flower, being the preferred upper limit for the number of paternal gametes that may be successfully used in this method, is known to the skilled person who is familiar with a specific crop. It is generally slightly higher than the average number of seeds present in a typical fruit of that crop. For tomato, for example, the average number of egg cells per flower is about 100, for Brassica species about 35, for Arabidopsis about 40-50, for watermelon about 200, for grape about 4, for cucumber about 250-300, for sweet pepper about 100, and for melon about 500. Burd et al., Am. J. Bot. 96(6), 1159-1167 (2009) describes a study on ovule number per flower in 187 angiosperm species.

A limited number of paternal gametes suitably may comprise any number that allows to use the method of the invention in an efficient way. This means that too much genetic variation in the male gametes must be avoided, i.e. the number of meiotic events that gave rise to the male gametes deposited onto a single stigma should be kept low if those meiotic events each generated a large degree of genetic rearrangements in the genome of the individual gametes that constitute the dyad or tetrad (through chromosome recombination).

In a preferred embodiment the limited number of paternal gametes is two or four (corresponding to the number of gametes comprised in a single pollen dyad or tetrad, respectively, and hence derived from a single meiosis in the absence or presence of the second meiotic division, respectively). This strategy will lead to the formation of four seeds (in case a tetrad was used for pollination) or two seeds (in case a dyad was used for pollination), which are genetically identical to the pollen grains that originated from a single meiotic division. When the gametes have the form of dyads, the limited number of paternal gametes that allows to use the method of the invention in an efficient way may be much higher than two, because the amount of genetic variation is greatly reduced, as the two gametes comprised within a dyad are genetically fully complementary to each other. Especially when using gametes that have the form of dyads it is thus efficient to use any number of gametes that is smaller than the average number of egg cells or ovules per flower.

The tetrad or dyad form of the male gametes is the result of interference with microspore tetrad separation in the father plant. In one embodiment, the interference with microspore tetrad separation may comprise interference with one or more target genes involved in the break-down of the pectin layer between the microspores resulting from a single meiotic division. The one or more target genes may be selected from the group consisting of QRT1, QR72, QRT3, or their functional homologues. Suitable mutations are the introduction of stop codons or frame shifts in the target genes, amino acid substitutions that disrupt protein structure and/or function, and insertions of genetic elements such as T-DNA into the coding sequence, promoter or other regulatory sequence of the gene. In Arabidopsis, the qrt1-4 mutation results from the insertion of a T-DNA into an exon of the QRT1 gene, the quartet mutant phenotype in the qrt1-5 mutant is caused by a T-DNA insertion into the QRT1 gene's promoter, and the qrt1-6 mutation is caused by a T-DNA insertion into an intron of the QRT1 gene. The qrt2-1 mutant in Arabidopsis may comprise a Valine to Alanine amino acid substitution on position 372 (a GTG to GCG mutation) in the QRT2 protein, which is the underlying cause of the quartet phenotype in this mutant line.

In another embodiment, interference with microspore tetrad separation may comprise interference with the breakdown of the pectin layer between the microspores resulting from a single meiotic division by chemical means. The QRT gene products are enzymes that play a role in the breakdown of the pectic polysaccharide (pectin) layer that is present between the individual male gametes (microspores) that arise from the meiotic division of a pollen mother cell. If this pectin layer is not degraded, the four male gametes (microspores) remain physically attached to each other in a tetrad form.

Interfering with one or more target genes involved in microspore tetrad separation may be achieved by a number of different approaches. The interfering with a target gene may consist of preventing transcription thereof. In one embodiment transcription of a target gene may be prevented by means of RNA oligonucleotides, DNA oligonucleotides or RNAi molecules directed against the target gene promoter.

In another embodiment transcription is prevented by means of the expression of a negatively acting transcription factor acting on the target gene promoter. Furthermore, the interfering with the target gene may also consist of destabilizing the target gene mRNA or transcript. This may be achieved by means of nucleic acid molecules that are complementary to the target gene mRNA or transcript, selected from the group consisting of antisense RNA, RNAi molecules, Virus-Induced Gene Silencing (VIGS) molecules, co-suppressor molecules, RNA oligonucleotides or DNA oligonucleotides.

Interfering with the target gene may also consist of inhibiting the target gene expression product, by means of one or more dominant negative nucleic acid constructs, or by means of one or more chemical compounds.

In yet another embodiment, the interfering with the target gene consists of the introduction of one or more mutations into the target gene, leading to perturbation of its biological function. The one or more mutations may either be introduced randomly—by means of one or more chemical compounds (such as ethyl methanesulphonate, nitrosomethylurea, hydroxylamine, proflavine, N-methyl-N-nitrosoguanidine, N-ethyl-N-nitrosourea, N-methyl-N-nitro-nitrosoguanidine, diethyl sulphate, ethylene imine, sodium azide, formaline, urethane, phenol, ethylene oxide) and/or physical means (such as UV-irradiation, fast-neutron exposure, X-rays, gamma irradiation) and/or insertion of genetic elements (such as transposons, T-DNA, retroviral elements)—or specifically, by means of homologous recombination or oligonucleotide-based mutation induction.

Chemical means to interfere with microspore tetrad separation comprise the use of chemical inhibitors that reduce the activity (or the stability) of the QRT gene products, or the use of chemicals that—directly or indirectly—reduce the expression level of the QRT gene products, resulting in the persistence of the pectin layer between the four microspores resulting from a single meiotic event. The enzyme activity of QRT proteins may be inhibited by means of chemical inhibitors, such that treatment of a flower bud during the stage of normal microspore separation (or a preceding stage) with the inhibiting chemical leads to the persistence of the pectin layer between the microspores that are derived from a single meiosis, and thus to the persistence of microspore tetrads during later developmental stages and at anthesis.

In a preferred embodiment, the father plant, which produced the said male gametes (in the form of a tetrad or a dyad) exhibits—in addition to the quartet phenotype—suppression of chromosome recombination, which abolishes chromosome crossing-over and leads to the intact transmission of entire chromosomes. In this embodiment the chance of identifying two genetically complementary genomes among the individual pollen grains of a tetrad is 50 percent. When the father plant which produced the said male gametes exhibits suppression of chromosome recombination, this suppression of chromosome recombination is achieved by interfering with one or more target genes involved in recombination.

In one embodiment the target gene is involved in double strand breaks, and it may be selected from the group consisting of SPO11, MER1, MER2, MRE2, MEI4, REC102, REC104, REC114, MEK1/MRE4, RED1, HOP1, RAD50, MRE11, XRS2, or their functional homologues.

In another embodiment the target gene is involved in chromosome pairing and/or strand exchange, and it may be selected from the group consisting of RHD54/TID1, DMC1, SAE3, RED1, HOP1, HOP2, REC8, MER1, MRE2, ZIP1, ZIP2, MEI5, RAD51, RAD52, RAD54, RAD55, RAD57, RPA1, SAMC3, SCC1, MASH2, MSH3, MASH6, PMS1, SOLODANCERS, HIM6, CHK2, or their functional homologues.

In yet another embodiment the target gene is involved in the meiotic recombination process, and it may be selected from the group consisting of SGS1, MSH4, MSH5, ZIP1 and ZIP2, or their functional homologues.

In another embodiment the target gene is selected from the group consisting of PRD1, PRD2, PIRD3, PHS1, NBS1, COM1, MND1, MER3/RCK, ZIP3, ZIP4, PTD, SHOC1, ZYP1, MLH1, MLH3, or their functional homologues.

Interfering with one or more target genes involved in recombination may be achieved by a number of different approaches. The interfering with a target gene may consist of preventing transcription thereof.

In one embodiment transcription of a target gene may be prevented by means of RNA oligonucleotides, DNA oligonucleotides or RNAi molecules directed against the target gene promoter. In another embodiment transcription is prevented by means of the expression of a negatively acting transcription factor acting on the target gene promoter. Furthermore, the interfering with the target gene may also consist of destabilizing the target gene mRNA or transcript. This may be achieved by means of nucleic acid molecules that are complementary to the target gene mRNA or transcript, selected from the group consisting of antisense RNA, RNAi molecules, Virus-Induced Gene Silencing (VIGS) molecules, co-suppressor molecules, RNA oligonucleotides or DNA oligonucleotides. Interfering with the target gene may also consist of inhibiting the target gene expression product, by means of one or more dominant negative nucleic acid constructs, or by means of one or more chemical compounds.

In yet another embodiment, the interfering with the target gene consists of the introduction of one or more mutations into the target gene, leading to perturbation of its biological function. The one or more mutations may either be introduced randomly—by means of one or more chemical compounds (such as ethyl methanesulphonate, nitrosomethylurea, hydroxylamine, proflavine, N-methyl-N-nitrosoguanidine, N-ethyl-N-nitrosourea, N-methyl-N-nitronitrosoguanidine, diethyl sulphate, ethylene imine, sodium azide, formaline, urethane, phenol, ethylene oxide) and/or physical means (such as UV-irradiation, fast-neutron exposure, X-rays, gamma irradiation) and/or insertion of genetic elements (such as transposons, T-DNA, retroviral elements)—or specifically, by means of homologous recombination or oligonucleotide-based mutation induction.

In another preferred embodiment, the father plant which produced the said male gametes exhibits—in addition to the quartet phenotype—second division restitution (SDR) during meiosis. In this embodiment, the father plant produces male gametes which are 2n and which have the form of dyads, because the second meiotic division does not take place. The two male gametes comprised within one dyad are genetically fully complementary, and the chance of identifying two genetically complementary genomes among the two individual pollen grains of a dyad is thus 100 percent.

When the father plant, which produced the said male gametes, exhibits second division restitution during meiosis, this second division restitution may occur spontaneously, without interference with the starting organism. In another embodiment, second division restitution is induced by means of genetic modification. This genetic modification may be transient, or it may be achieved by stable incorporation into the genome of a genetic element (such as a transgene, mutation, transposon, retroviral element, T-DNA) increasing the number of second division restitution events in the organism.

In yet another embodiment second division restitution is achieved by subjecting the father plant to environmental stress, such as temperature stress, $NO_2$, nitrous oxide ($N_2O$), or combinations thereof (Zhang et al. (2002) *Journal of Horticultural Science & Biotechnology* 78: 84-88; WO 2006/094773; Barba-Gonzalez et al. (2006), *Euphytica* 148: 303-309; Okazaki et al. (2005), *Euphytica* 143: 101-114).

The loss of maternal chromosomes from the zygote—to obtain a seed set containing a limited number of seeds in which the maternal chromosomes are absent—may be achieved in different manners. In one embodiment, a haploid inducer line may be used as the female. A haploid inducer line is a plant in which the chromosomes of one of the parents are eliminated from the genome of the zygote formed after fertilization of an egg cell by pollen. The female may e.g. be a plant of a different species, as has been described by e.g. Bains & Howard 1950, *Nature* 166: 795. In another embodiment the loss of maternal chromosomes from the zygote results from the use of a transgenic plant as the mother organism, which transgenic plant may comprise a heterologous transgene expression cassette, the expression cassette which may comprise a promoter operably linked to a polynucleotide encoding a recombinantly altered CENH3, CENPC, MIS12, NDC80 or NUF2 polypeptide, and having a corresponding inactivated endogenous CENH3, CENPC, MIS12, NDC80 or NUF2 gene as described in US patent application 20110083202 and WO2011/044132.

The present invention also relates to a set of seeds containing a limited number of seeds in which the maternal chromosomes are absent, which set is composed of pairs of essentially genetically complementary seeds which when crossed result in essentially the same hybrid, and which set of seeds is obtainable by the method of the invention. The seeds of this set of seeds all have the same father, because they originated from the pollination of a mother plant with a limited number of paternal gametes that have the form of tetrads or dyads, which paternal gametes had been collected from a single father plant. Because of this, and because of the elimination of the maternal chromosomes from the zygotes, from a genetic point of view the seeds of the said set of seeds only have one male grandparent and one female grandparent, namely the parents of their father. This is schematically represented in FIG. 4.

The present invention also relates to a set of parent plants for the production of a plant of which the genetic constitution is essentially identical to the genetic constitution of its male grandparent, which may comprise growing plants from seeds of the set of seeds of the invention, after or prior to doubling the chromosome number of the seeds, and identifying two genetically complementary plants as the parent plants. Such genetically complementary plants may be identified by means of molecular (genetic) markers for which the father plant (who produced the male gametes) was heterozygous, and for which the two paternal grandparents had different alleles. These markers may be scored with a number of different approaches, such as direct DNA-sequencing of specific genomic regions, AFLP, RFLP, SSR, RAPD, KASPar (KBioscience), Invader™ or Invader Plus™ (see e.g. De Vienne ed. (2003) Molecular Markers in Plant Genetics and Biotechnology. Science publishers Inc. Enfield, N.H. USA. ISBN 1-57808-239-0).

The invention further relates to a method for screening the set of seeds or the plants grown thereof for their genetic constitution, to identify a plant of which the genetic constitution is essentially identical to the genetic constitution of its paternal grandfather, and to identify another plant of which the genetic constitution is essentially identical to the genetic constitution of its paternal grandmother.

A plant of which the genetic constitution is essentially identical to the genetic constitution of its paternal grandfather may subsequently be crossed to another plant of which the genetic constitution is essentially identical to the genetic constitution of its paternal grandmother, in order to obtain progeny plants of which the genetic constitution is essentially identical to the genetic constitution of their own grandfather. With 'their own grandfather' the (hybrid) plant is meant, which produced the pollen tetrads or pollen dyads that were used for pollination of the haploid inducer line. This pedigree is graphically illustrated and clarified in FIG. 4.

The invention further relates to the use of the said set of seeds, after or prior to doubling the chromosome number of the seeds, for the identification of two genetically complementary plants as the parents for a cross.

Crop species on which this invention may be practised include for example tobacco, poplar, sugar beet, oilseed rape, soybean, tomato, cucumber, gherkin, corn salad, spinach, pepper, petunia, potato, eggplant, melon, watermelon, carrot, radish, vegetable *Brassica* species (cabbage, cauliflower, broccoli, kohlrabi, Brussels sprouts), bean, pea, onion, strawberry, table beet, asparagus, and grape vine.

The present invention is further described in the following numbered clauses.

1. A method for the production of a set of seeds which are genetically identical to the male gametes from which they arise, comprising:
   a) placing a limited number of paternal gametes that have the form of tetrads or dyads on the stigma of a flower to fertilize maternal egg cells to obtain a number of zygotes;
   b) inducing the loss of maternal chromosomes from the zygotes to obtain a seed set containing a limited number of seeds in which the maternal chromosomes are absent.
2. A method according to clause 1, wherein the limited number of paternal gametes is equal to or lower than the number of egg cells contained in the female reproductive organ carrying the stigma.
3. A method according to clause 1 or 2, wherein the limited number of paternal gametes is two or four.
4. A method according to any combination of the clauses 1-3, wherein the paternal gametes that have the form of tetrads or dyads are the result of interference with microspore tetrad separation.
5. A method according to clause 4, wherein interference with microspore tetrad separation comprises interference with one or more target genes involved in the break-down of the pectin layer between the microspores resulting from a single meiotic division.
6. A method according to clause 5, wherein the one or more target genes are selected from the group consisting of QRT1, QRT2, QRT3, or their functional homologues.
7. A method according to clause 4, wherein interference with microspore tetrad separation is achieved by chemical means.
8. A method according to any combination of clauses 1-7, wherein the father plant exhibits suppression of chromosome recombination.
9. A method according to any combination of the clauses 1-7, wherein the father plant exhibits second division restitution (SDR) during meiosis.
10. A method according to clause 8, wherein suppression of chromosome recombination is achieved by interfering with one or more target genes involved in recombination.
11. A method according to clause 10, wherein the target gene is involved in double strand breaks.
12. A method according to clause 11, wherein the target gene is selected from the group consisting of SPO11, MER1, MER2, MRE2, MEI4, REC102, REC104, REC114, MEK1/MRE4, RED1, HOP1, RAD50, MRE11, XRS2, or their functional homologues.
13. A method according to clause 10, wherein the target gene is involved in chromosome pairing and/or strand exchange.
14. A method according to clause 13, wherein the target gene is selected from the group consisting of RHD54/TID1, DMC1, SAE3, RED1, HOP1, HOP2, REC8, MER1, MRE2, ZIP1, ZIP2, MEI5, RAD51, RAD52, RAD54, RAD55, RAD57, RPA, SMC3, SCC1, MSH2, MSH3, MSH6, PMS1, SOLODANCERS, HIM6, CHK2, or their functional homologues.
15. A method according to clause 10, wherein the target gene is involved in the meiotic recombination process.
16. A method according to clause 15, wherein the target gene is selected from the group consisting of SGS1, MSH4, MSH5, ZIP1 and ZIP2, or their functional homologues.
17. A method according to clause 5 and/or 10, wherein the interfering with the one or more target genes consists of preventing transcription thereof.
18. A method according to clause 17, wherein transcription is prevented by means of RNA oligonucleotides, DNA oligonucleotides or RNAi molecules directed against the target gene promoter.

19. A method according to clause 17, wherein transcription is prevented by means of the expression of a negatively acting transcription factor acting on the target gene promoter.
20. A method according to clause 5 and/or 10, wherein the interfering with the one or more target genes consists of destabilizing the target gene mRNA or transcript.
21. A method according to clause 20, wherein the target gene mRNA is destabilized by means of nucleic acid molecules that are complementary to the target gene mRNA or transcript, selected from the group consisting of antisense RNA, RNAi molecules, Virus-Induced Gene Silencing (VIGS) molecules, co-suppressor molecules, RNA oligonucleotides or DNA oligonucleotides.
22. A method according to clause 5 and/or 10, wherein the interfering with the one or more target genes consists of inhibiting the target gene expression product.
23. A method according to clause 22, wherein the target gene expression product is inhibited by means of the expression product(s) of one or more dominant negative nucleic acid constructs.
24. A method according to clause 22, wherein the target gene expression product is inhibited by means of one or more chemical compounds.
25. A method according to clause 5 and/or 10, wherein the interfering with the one or more target genes consists of the introduction of one or more mutations into the target gene, leading to perturbation of its biological function.
26. A method according to clause 25, wherein the one or more mutations are introduced randomly by means of one or more chemical compounds and/or physical means and/or insertion of genetic elements.
27. A method according to clause 26, wherein the one or more chemical compounds are selected from the group consisting of ethyl methanesulphonate, nitrosomethylurea, hydroxylamine, proflavine, N-methyl-N-nitrosoguanidine, N-ethyl-N-nitrosourea, N-methyl-N-nitro-nitrosoguanidine, diethyl sulphate, ethylene imine, sodium azide, formaline, urethane, phenol and ethylene oxide.
28. A method according to clause 26, wherein the physical means are selected from the group consisting of UV-irradiation, fast-neutron exposure, X-rays, gamma irradiation.
29. A method according to clause 26, wherein the genetic element is selected from the group consisting of transposons, T-DNA, retroviral elements.
30. A method according to clause 25, wherein the one or more mutations are introduced specifically by means of homologous recombination or oligonucleotide-based mutation induction.
31. A method according to clause 9, wherein second division restitution occurs spontaneously, in particular without interference with the starting organism.
32. A method according to clause 9, wherein second division restitution is induced by means of genetic modification.
33. A method according to clause 32, wherein the genetic modification is transient.
34. A method according to clause 32, wherein the genetic modification is achieved by stable incorporation into the genome of a genetic element increasing the number of second division restitution events in the organism.
35. A method according to clause 9, wherein second division restitution is achieved by subjecting the father plant to environmental stress.
36. A method according to clause 35, wherein the environmental stress is selected from temperature stress, $NO_2$, nitrous oxide ($N_2O$), or combinations thereof.
37. A method according to any combination of the clauses 1-36, wherein the loss of maternal chromosomes from the zygote is induced by using a haploid inducer line as the female.
38. A method according to clause 37, wherein the female is a plant of a different species.
39. A method according to any combination of clauses 1-37, wherein the female plant is a transgenic plant that comprises a heterologous transgene expression cassette, the expression cassette comprising a promoter operably linked to a polynucleotide encoding a recombinantly altered CENH3, CENPC, MIS12, NDC80 or NUF2 polypeptide, and having a corresponding inactivated endogenous CENH3, CENPC, MIS12, NDC80 or NUF2 gene.
40. Set of seeds containing a limited number of seeds in which the maternal chromosomes are absent, which set is composed of pairs of genetically complementary seeds which when plants grown from the seeds are crossed result in essentially the same hybrid, and which seed set is obtainable by a method according to any combination of clauses 1-39.
41. A method for providing a set of parent plants for the production of a plant of which the genetic constitution is essentially identical to the genetic constitution of its male grandparent, comprising growing plants from seeds of the set of seed according to clause 40, after or prior to doubling the chromosome number of the seeds, and identifying two genetically complementary plants as the parent plants.
42. A method according to clause 41, wherein the set of seeds or the plants grown thereof are screened for their genetic constitution, to identify a plant of which the genetic constitution is essentially identical to the genetic constitution of its paternal grandfather, and to identify another plant of which the genetic constitution is essentially identical to the genetic constitution of its paternal grandmother.
43. A method according to any combination of clauses 40-42, wherein a plant of which the genetic constitution is essentially identical to the genetic constitution of its paternal grandfather, is crossed to another plant of which the genetic constitution is essentially identical to the genetic constitution of its paternal grandmother, in order to obtain progeny plants of which the genetic constitution is essentially identical to the genetic constitution of their own grandfather.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Identification of Quartet-Pollen-Shedding *Brassica* Plants

An essential resource for carrying out this invention is a plant of the species of interest that sheds its pollen grains in a tetrad form, whereby the four products from a meiotic division remain physically attached to each other. Such a plant can either be obtained in a mutant screen or through a transgenic approach. This example illustrates the first option, while the second option will be explained in subsequent examples.

In order to identify a plant exhibiting the quartet pollen phenotype, *Brassica oleracea* EMS-mutant population was screened phenotypically, to detect the occurrence of pollen grains with the quartet phenotype (i.e. pollen tetrads) in the anthers of individual plants. In a bulk-approach, pollen from multiple plants was pooled together and diluted in solution so that individual pollen grains could be clearly discerned. These pollen pools were then screened by eye under a binocular, but alternatively this screen is also possible with flow cytometry or by filtration (with a filter that has a pore size that is larger than the diameter of an individual pollen grain, but smaller than the diameter of a pollen tetrad). Upon detecting the desired quartet phenotype in a pollen pool, all plants that contributed pollen to that pool were screened individually, until a quartet mutant plant was positively identified. In the next generation the transmissibility of the quartet phenotype was confirmed.

Example 2

Creating a *Brassica* Plant that Eliminates the Maternal Genome from its F1-Progeny A publication by Maruthachalam & Chan (*Nature* 464, 615-619; 2010) teaches that the transformation of *Arabidopsis thaliana* cenh3 mutant plants with an overexpression construct for a GFP-CENH3-tailswap protein results in an aberrant mitotic division in the zygote, following fertilization. During this aberrant mitosis the maternal chromosomes are selectively eliminated from the dividing zygote. As the CENH3 protein is universal in eukaryotes and its function is very well conserved this strategy from *Arabidopsis* is widely applicable in other plant species.

In order to create a *Brassica oleracea* plant in whose F1 progeny the maternal genome is selectively eliminated, a *Brassica* plant was created that lacks a functional version of the protein that is orthologous to CENH3 from *Arabidopsis*. This was achieved by means of an RNAi approach. This plant was subsequently genetically transformed by means of *Agrobacterium* infection, with the GFP-CENH3-tailswap construct described by Maruthachalam & Chan (*Nature* 464, 615-619; 2010) and US patent application 20110083202. Due to the lethality of the homozygous cenh3 mutant plant (as is the case in *Arabidopsis*), it was necessary to transform a heterozygous silenced plant with this construct. Transformant plants were subsequently selected based on the construct's selection marker, and the presence and correct expression of the GFP-CENH3-tailswap fusion protein could be detected with fluorescence microscopy during mitotic division.

Example 3

Combining the Quartet Phenotype with Maternal Genome Elimination in *Arabidopsis*

This example illustrates how the genotype of a hybrid plant may be efficiently reconstituted.

A transgenic *Arabidopsis thaliana* plant of the Ler accession was created, harbouring a single copy (in homozygous state) of an RNAi construct that targets the QRT1 gene (At5g55590), driven by the CaMV 35S constitutive promoter. See, e.g., NCBI Reference Sequence: NC_003076.8, the reference assembly of the QRT1 gene (At5g55590), reproduced below as SEQ ID NO: 1.

```
  1 gctacataga gaggctccaa gtatttatta aactcatctt tctcacacga
    cctttcacct
 61 ccaaagactc ccaacaaaaa tcataataaa gaaatacaaa aacg-
    taaact ttgccaagtt
121 tttttttctt cctttctta actctctcac tcccacgaat tcgtgagaag
    aaaccttaaa
181 acgttttttt tccagagcac gaaaaaactc cccacctcac ttaaactttt
    ttccttgtgc
241 aggagacatc attccccatg aaagtcgaag cttttattcc cgccgttta
    ttgctctgtt
301 ttggggtaat gttatgttta aaaagctcgt gtgcgttgca gataggtaac
    aataatgagt
361 tgaagaatta cataagttgg gaagatttga gagttgtgga agatg-
    gaaga atagagagaa
421  gttttagcat  taaggagaat  agtaattggg  taaccacaaa
    cgctaacgct aacgcgaacg
481 ctactaacgt gagaagagtg attgtggttg ataaaaacgg aggag-
    gagat tctgttacag
541 ttcaaggagc tgttgatatg gttcctgatt ccaattcaca gagagttaaa
    atcttcattc
601 ttcctgggat ttacaggtaa cttacaaaaa aagatttaag acataaaccg
    tgtttgtttt
661 tttctttgta tgttattaat ctttgagaaa cgtctttggg agtgtggggt
    tttgtttccg
721 aagatttcgt ttttttttt gttttttttt ggtgtgataa aagcagttga
    agctaaattc
781 ttgggttagt gggataatct aagcataagc tgcttacgta aataaaatcg
    tgggtctcaa
841 gaatctttgt ctgtaaaacc gtagaataag aatctttgtc tttgttatat
    actctgttct
901 tttttgtca  gaatctttgt  ctttgttatc  tactcttgtt  tttttcttc
    agaatctctt
961 ctctgctatg tgttgtttgc agggagaagg tgattgtgcc gaaat-
    caaaa ccgtatattt
1021 cgttcatagg taatgagagc tatgcgggag atacagtgat tagttg-
    gagc gataaagctt
1081 cagaccttgg ctgcgatggt aaagaactcg gcacttatag aaccgc-
    ctct gtttccattg
1141 aatctgattt cttctgtgct actgccatca cttttgaggt cctaaaaccc
    tctcttttac
1201 tattattcct tgtctacttt ctatgtgtat tgtgttttta tgttttgaat tgttt-
    gtgat
1261 gtacggattg aggcagaaca cggtggttgc agaggcaggg
    gaacagggga ggcaagcggt
1321  ggcgttgaga  ataattgggg  acaaagctgt  gttctataga
    gttagggttt tgggatcaca
1381 agacactctt tttgatgaca atggatctca ctacttttac caatgctata
    tccaaggcaa
1441 tgtagatttc atctttggca atgcgaaatc actttaccag gcaaaac-
    ccc ttccatttga
1501 tcttcttaaa tcctttgtat cgaaatccat ttgtaaagat attgatcgaa
    gttttggtgt
1561 tggtaaacca caggactgtg atatccactc aaccgcaaag aga-
    tatggcg cgatcgcggc
```

1621 tcatcataga gactcggaga ctgaagatac cgggttctcc tttgt-
gaact gtgatatcag
1681 tggtactggg cagatttact taggaagggc ttggggaaac tact-
caagaa ctgtttattc
1741 aaactgtttc atagctgata ttatcactcc tgtgggctgg agt-
gactgga aacaccctga
1801 gaggcaaagg taaaaaaagg atcttgaaaa ttgaaaactc atctct-
gaaa ctacagcatt
1861 tctctctcaa aacaacatca agcgaatttc ttttgcagga aagtgatgtt
cggggagtac
1921 aattgcaggg gaagaggagc agagagagga ggccgagtac
cgtggtcgaa aactcttacc
1981 agagatgaag tgaagcctt tctgggaaga gagttcatat atgga-
gatca atggctgaga
2041 ctctaaatcc tttttcaacc ggacataaag gtccagctag ctaaca-
ggag atgatgatct
2101 aattctactc tattcatttg taattagttt gaatttagag agaaatagaa
tctgcatgtt
2161 ttaactcata ccaaagtaaa tgaaacccag gttttggttt tagat Alternatively other techniques such as artificial microRNAs (amiRNAs) may be used for this purpose. This plant was then crossed to a wild-type *Arabidopsis thaliana* plant of the Ws accession.

The resulting F1 generation consisted of hybrid plants with a mixed Ler/Ws background, which were hemizygous for the RNAi construct. Because the RNAi construct acts sporophytically and in a dominant manner, all F1 plants exhibited the quartet pollen phenotype. An F1 plant—exhibiting the quartet pollen phenotype—was then crossed as a father with an *Arabidopsis thaliana* cenh3 mutant plant of the Col-0 accession, which had been genetically transformed with the GFP-CENH3-tailswap construct as reported by Maruthachalam & Chan (*Nature* 464, 615-619; 2010) and US patent application 20110083202. This cross resulted in the elimination of the maternal chromosomes during the first mitotic division in the zygote, leading to the formation of haploid seeds.

In preparation for the crossing, nearly dehiscent anthers of the father plant were opened under a binocular microscope to allow the collection of individual, ripe pollen tetrads. Each pollen tetrad was carefully deposited onto the pistil of a mother plant, using an eyelash or a fine brush hair, and the four pollen grains were allowed to fertilize four ovules. The four seeds resulting from this limited pollination with a single pollen tetrad were allowed to mature, and were subsequently harvested and allowed to germinate. Alternatively, more than one tetrad may be deposited onto the pistil of the mother plant, but care should be taken that the number of pollen grains does not exceed the average number of ovules in the female reproductive part of the species. The use of more than one tetrad for pollination will namely reduce the efficiency with which genetically complementary progeny plants may be identified.

The ploidy of the seedlings resulting from the limited pollination of the transgenic Col-0 mother plant was tested by flow cytometry. Their ploidy was n, except in some cases in which spontaneous genome doubling to 2n had meanwhile occurred. For haploid individuals genome doubling was subsequently accomplished by standard methods known to the skilled person (e.g. colchicine treatment). Once the four seedlings resulting from this cross were 2n, their genomic DNA was isolated and genetically analysed for genetic markers covering the entire *Arabidopsis* genome. Especially markers polymorphic between Col-0 and Ler and between Col-0 and Ws were tested, to distinguish the contribution of both parental genomes to the four progeny plants. Due to the elimination of the maternal genome from the zygotes the four progeny plants only contained recombined chromosomes from the hybrid father plant, and hence they tested negative for all Col-0-specific markers.

FIG. 2 shows that the occurrence rate of progeny plants with a certain number of complementary chromosomes within a pollen tetrad is dependent on the haploid chromosome number (n). *Arabidopsis* has five chromosomes, and because of the quartet pollen phenotype in the original father plant the chromosome constellation of the four seedlings results from a single meiotic division. This implies that there is a theoretical chance of 1 in 16 (6.3%) for two fully complementary genomes to be present in a single pollen tetrad. The chance is 31.3% for having two genomes that have one non-complementary chromosome, and 62.5% for having two genomes that have two non-complementary chromosomes. In all cases the individual pollen grains in a tetrad are therefore at least 50% complementary to each other. Importantly, if recombination results in e.g. 40% heterozygosity, the overall complementarity between the genome of the individual pollen grains will always be higher than 50%, because even the "non-complementary" chromosomes would then still be 60% complementary to each other.

Therefore, in theory only 16 individual crosses with a pollen tetrad are required on average to identify two *Arabidopsis* seedlings that have essentially complementary sets of chromosomes. In practice, however, more are needed because the efficiency of the pollination, seed formation, and plant germination and survival is generally below 100 percent. As a rule of thumb 10 times more crosses were done with single tetrads, i.e. 160 in this case, to maximize the chance of success.

After identification, two genetically essentially complementary plants were grown to anthesis and then crossed. The genetic constitution of the F1 progeny resulting from this cross was experimentally shown to be essentially identical to the genetic constitution of its paternal grandfather, i.e. the qrt1 mutant plant with a Ler/Ws hybrid background.

Example 4

Combination of the Quartet Phenotype with Maternal Genome Elimination in *Arabidopsis*, with Non-Transgenic Progeny In Example 3 the F1 progeny remained transgenic, because it retained the RNAi construct targeting the QRT1 gene, and hence also the quartet pollen phenotype. However, when a GFP reporter cassette that specifically expresses the Green Fluorescent Protein in mature pollen grains is integrated into the RNAi construct used in Example 3, this allows another approach, in which the progeny plants are not transgenic. The T-DNA construct then also contains a GFP protein with a nuclear localization signal under a late-pollen-specific promoter (the LAT52 promoter; Twell et al, 1990, *Development* 109: 705-713), which allows the easy visual detection of this construct in mature pollen grains.

In anther squashes of the Ler/Ws hybrid plant mentioned in Example 3 (hemizygous for the RNAi construct targeting QRT1), pollen tetrads were selected in which two of the four pollen grains did not express GFP in their nucleus, either visually (using a fluorescence binocular or microscope) or by FACS (fluorescence-activated cell sorting). Only two of the four pollen grains thus contained the RNAi construct targeting the QRT1 gene. Pollination of the above-mentioned Col-0 mother plant—which induced the elimination of the maternal chromosomes during the first mitotic division in the zygote—with such a pollen tetrad gave rise to two transgenic haploid progeny plants (harbouring the RNAi construct) and to two non-transgenic haploid progeny plants (not harbouring the RNAi construct).

The non-transgenic progeny plants per definition lacked the Ler chromosome fragment harbouring the RNAi-construct for QRT1, and the crossing of these two plants may thus never lead to the exact reconstitution of the original F1 hybrid, because the reconstituted plants will be homozygous for at least one Ws chromosome region, namely for the chromosome region which corresponds to the chromosome region that contains the RNAi-construct for QRT1 in the Ler parent plant.

Example 5

Combining the Quartet Pollen Phenotype with Second Division Restitution in Sweet Pepper (*Capsicum annuum*)

When second division restitution (SDR) occurs, the second meiotic division does not take place, and the result of meiosis will be two diploid pollen grains, instead of four haploid pollen grains. Therefore, when the meiotic products remain physically attached to each other—as is the case with the quartet pollen phenotype—a plant will produce pollen dyads when SDR occurs. In this preferred embodiment of the current invention, the two diploid meiotic products remain physically attached to each other, and because their chromosomes have identical recombination break points the two pollen grains are 100% genetically complementary to each other.

A sweet pepper plant (*Capsicum annuum*) exhibiting the quartet pollen phenotype was obtained through an RNAi approach, similarly as described in Example 3. A progeny plant thereof—homozygous for the quartet phenotype—was subjected to cold stress, in order to increase the frequency of unreduced microspore (gamete) formation, as described by Zhang et al. (2002) *Journal of Horticultural Science & Biotechnology* 78: 84-88 and in example 2 of WO 2006/094773). Up to 25% of the microspores and pollen produced in the anthers of the cold-treated plant had the form of a dyad. Isolated microspore fractions were further enriched for dyads by microscopic analysis (alternatively flow cytometry may be used). Using this approach, the application referred to as Near-Reverse Breeding (WO 2006/094773) could be enabled in a preferred embodiment.

For this purpose, a second sweet pepper plant was created which eliminates the maternal genome from its zygotes during the first mitotic division, following the experimental approach outlined in Example 2. This transgenic sweet pepper plant was pollinated with a single pollen dyad derived from the above-mentioned cold-treated sweet pepper plant, and the resulting two diploid seeds were harvested and germinated. The pollen dyad was selected manually in an anther squash from among the pollen quartets that resulted from non-SDR meiotic events.

The plants grown from these two diploid seeds were subsequently crossed, and—using genetic markers—the genetic composition of the progeny plants of this cross could be confirmed as being essentially identical to the genetic composition of the sweet pepper plant that produced the pollen dyad we used for pollination. However, due to cross-over events that had occurred during the formation of the pollen dyads some telomeric variation had been introduced, which provided additional genetic variation in the selected hybrid background.

Thus, the sweet pepper plant created in this example by pollinating a haploid inducer mother plant with a pollen dyad produced by another sweet pepper plant was genetically only "essentially identical" to the sweet pepper plant that produced the pollen dyad for pollination, because additional genetic variation had been introduced at the telomeres, as a result of cross-over events that had occurred during the formation of the pollen dyads. All genetic material of the father plant had been maintained, but some parts of it had been rearranged through cross-over events, and this rearrangement may cause additional phenotypic effects.

This example thus allows for the introduction of additional genetic variation in a selected (elite) hybrid plant. This additional variation may have positive or negative additional phenotypic effects, when compared to the original hybrid phenotype, and it thus provides an interesting opportunity to further improve (and/or fine-tune) a hybrid phenotype, without losing the combination of selected traits comprised in the original hybrid.

Alternatively, the sweet pepper plant exhibiting the quartet phenotype may be crossed with a sweet pepper plant that naturally exhibits an above-average degree of SDR. Their progeny will then naturally produce an above-average percentage of pollen dyads. Another strategy is to mutagenize a population of sweet pepper plants that naturally exhibit an above-average degree of SDR, and to screen for plants displaying the quartet pollen phenotype in this mutant population, in a forward genetics approach.

In each and every dyad the chance is 100% that the two pollen grains are genetically essentially complementary to each other (with identical chromosomal break-points). The two microspores comprised in a dyad are per definition genetically essentially complementary, and crossing the two plants that may be derived from any one of these dyads will always result in a hybrid plant that is essentially genetically identical to the original hybrid plant that produced the dyads. This embodiment thus greatly improves the efficiency of the Near Reverse Breeding technology.

Generally, in this embodiment of the invention a plant carrying a genetic feature that causes the elimination of the maternal chromosomes from its F1-progeny is pollinated through limited pollination. The pollen used in this cross is a single pollen dyad obtained from a hybrid plant of the same species, which exhibits the quartet pollen phenotype in combination with SDR. This pollen dyad is obtained by visually screening squashed anthers and by subsequently selecting a dyad constellation from among the tetrad constellations (which resulted from meiotic divisions during which SDR had not occurred), or by enriching a pollen fraction for dyads—in a more high-throughput setting—by means of flow cytometry or cell sorting.

After pollination of the mother plant carrying a genetic feature that causes the elimination of the maternal chromosomes from its F1-progeny, each of the two diploid pollen grains comprised in the dyad fertilise an ovule, and seed is allowed to form and mature. Upon ripeness the two seeds resulting from this cross are harvested and germinated. The resulting seedlings are then tested for their ploidy level by means of flow cytometry, to confirm that they are indeed 2n, as would be expected.

Subsequently, genomic DNA is isolated from the two seedlings, and genetic markers covering the entire genome are tested in both individuals. Due to the elimination of the maternal chromosomes from the zygote, both seedlings are expected only to possess paternal chromosomes. Due to the fact that the chromosomes from both seedlings originated in a single meiotic division, all chromosome break points are identical, and their genomes are 100% complementary. This is confirmed by the genome-wide marker analysis.

The seedlings are subsequently grown to maturity and crossed with each other. Their F1 progeny is genetically essentially identical to the original starting hybrid plant that was used as a father in the first cross, except for cross-over events that have occurred during the formation of the SDR gametes. These cross-over events introduce some telomeric variation, which provides additional genetic variation in the selected hybrid background.

The near-exact reconstruction of the (hybrid) genotype of the paternal grandfather organism was achieved in only two generations' time and without the need for intermediate regeneration or genome doubling steps or tissue culture.

Example 6

Combining the Quartet Pollen Phenotype with Suppression of Chromosome Recombination and Maternal Genome Elimination in *Arabidopsis*

From a cross between an *Arabidopsis* plant that exhibits the quartet pollen phenotype and another *Arabidopsis* plant in which chromosome recombination is partially or completely suppressed (either by transgenic, mutational or chemical means), an F2 progeny plant may be selected in which both properties are combined: the four pollen grains resulting from a single meiotic division remain physically attached to each other up to the time of anthesis and pollen shedding, and during meiosis the recombination of homologous chromosomes is suppressed.

This progeny plant allows the application of Reverse Breeding (WO 03/017753; Dirks et al 2009) in a more efficient way. Because the meiotic products remain physically attached to each other, the chance of identifying two pollen grains with essentially complementary sets of chromosomes is greatly increased. The number of different tetrads is a function of the chromosome number of the species, but within a single tetrad, however, the chance that two pollen grains have fully complementary sets of chromosomes is always 50%, as the four pollen grains are pairwise complementary. Within each and every tetrad the chance of finding two pairs of complementary pollen grains is thus 100%.

As described in Example 3, an *Arabidopsis thaliana* Ler plant was created, harbouring a single copy (in homozygous state) of an RNAi construct that targets the QRT1 gene, driven by the CaMV 35S constitutive promoter. This plant was then crossed with an *Arabidopsis thaliana* plant of the Ws accession which harboured a homozygous single copy of an RNAi construct that targets the DMC1 gene, also driven by the CaMV 35S constitutive promoter.

The resulting F1 generation consisted of hybrid plants with a mixed Ler/Ws background, which were all hemizygous for both RNAi constructs. Because the RNAi constructs both function sporophytically and in a dominant manner, the F1 plants exhibited the quartet pollen phenotype and suppression of chromosome recombination during meiosis. As an undesired side-effect the suppression of chromosome recombination also resulted in the occurrence of unbalanced pollen tetrads (alongside balanced tetrads), because in the absence of sufficient functional DMC1 protein each chromosome is randomly distributed over the daughter cells of a division. However, balanced tetrads could be selected from anthers experimentally (through visual inspection and/or flow cytometry).

Balanced pollen tetrads derived from an F1 plant— exhibiting the quartet pollen phenotype in combination with suppression of chromosome recombination, being hemizygous for both transgenic constructs—were subsequently used to pollinate *Arabidopsis thaliana* cenh3 mutant plants of the Col-0 accession (as created and reported by Maruthachalam & Chan, 2010 and US patent application 20110083202), which had been genetically transformed with the GFP-CENH3-tailswap construct reported by Maruthachalam & Chan (2010) and US patent application 20110083202, which results in the elimination of the maternal chromosomes during the first mitotic division in the zygote.

When a single balanced pollen tetrad was used for pollination of a pistil of the mother plant, this cross ideally resulted in four haploid progeny seeds. The four progeny seeds were allowed to germinate, and the seedlings were genetically tested with markers. Because no chromosome recombination had occurred during meiosis (due to the RNAi construct targeting DMC1 all chromosomes were passed onto the next generation in their entirety), only very few markers needed to be tested for each chromosome, to determine whether it was inherited from the Ler grandparent or from the Ws grandparent (in fact a single polymorphic marker per chromosome would be sufficient; in our experimental approach we used one marker per chromosome arm, i.e. two markers per chromosome).

To ensure that the mother plant had not contributed genetically to the progeny also Col-0 specific markers were tested, but no Col-0 genetic material could be identified, as was also the case in Example 3.

The four progeny plants were found to be pairwise perfectly genetically complementary, and based on the genetic marker analysis these pairs could be efficiently identified. Crossing such a pair of genetically complementary progeny plants to each other resulted in the efficient genetic reconstitution of the original hybrid plant that produced the pollen tetrad that was used for pollination, i.e. the Ler/Ws hybrid plant hemizygous for both RNAi constructs. FIG. 4 illustrates the pedigree of the plants used in this experiment.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for the production of a set of *Arabidopsis* seeds which are genetically identical to the male gametes from which they arise, comprising:
   a) placing two or four paternal gametes from *Arabidopsis* that have the form of tetrads or dyads on the stigma of an *Arabidopsis* flower to fertilize maternal egg cells, to obtain a number of zygotes;
   b) inducing the loss of maternal chromosomes from the zygotes to obtain a seed set containing a limited number of seeds in which the maternal chromosomes are absent,
   wherein the two or four paternal gametes is equal to or lower than the number of egg cells contained in the female reproductive organ attached to the stigma and
   wherein the loss of maternal chromosomes from the zygote is induced by using a haploid inducer line as the female, wherein the female is a transgenic plant comprising a heterologous transgene expression cassette comprising a promoter operably linked to a polynucleotide encoding a recombinantly altered CENH3 polypeptide, and having a corresponding inactivated endogenous CENH3 gene,
   wherein the paternal gametes that have the form of tetrads or dyads result from interference with microspore tetrad separation and
   wherein interference with microspore tetrad separation comprises interference with a QRT1 gene.

2. The method as claimed in claim 1, wherein the paternal gametes are produced by a father plant which exhibits second division restitution (SDR) during meiosis.

3. The method as claimed in claim 1, wherein the interfering with the QRT1 gene prevents transcription thereof.

4. The method as claimed in claim 1, wherein the interfering with the QRT1 gene consists of destabilizing the QRT1 gene mRNA or transcript.

5. The method as claimed in claim 1,
   wherein the interfering with the QRT1 gene consists of introducing one or more mutations into the QRT1 gene, leading to perturbation of its biological function,
   wherein the one or more mutations are introduced randomly by one or more chemical compounds, by physical means, or by insertion of a genetic element, or
   wherein the one or more mutations are introduced specifically by homologous recombination or oligonucleotide-based mutation induction.

6. The method as claimed in claim 4,
   wherein the destabilizing the QRT1 gene mRNA or transcript is by binding with antisense RNA, RNAi molecules, Virus-Induced Gene Silencing (VIGS) molecules, co-suppressor molecules, RNA oligonucleotides or DNA oligonucleotides.

7. The method as claimed in claim 5,
   wherein the one or more chemical compounds is ethyl methanesulphonate, nitrosomethylurea, hydroxylamine, proflavine, N-methyl-N-nitrosoguanidine, N-ethyl-N-nitrosourea, N-methyl-N-nitro-nitrosoguanidine, diethyl sulphate, ethylene imine, sodium azide, formaline, urethane, phenol or ethylene oxide, or
   wherein the physical means are UV-irradiation, fast-neutron exposure, X-rays, gamma irradiation, or
   wherein the genetic element is a transposon, T-DNA or retroviral element.

8. The method as claimed in claim 2, wherein second division restitution is achieved by subjecting the father plant to environmental stress wherein the environment stress is temperature stress, $NO_2$, nitrous oxide ($N_2O$), or a combination thereof.

* * * * *